United States Patent [19]

Stockel

[11] Patent Number: 5,366,694
[45] Date of Patent: * Nov. 22, 1994

[54] ONE-STEP CONTACT LENS STERILIZATION PROCESS

[76] Inventor: Richard F. Stockel, 475 Rolling Hills Rd., Bridgewater, N.J. 08807

[*] Notice: The portion of the term of this patent subsequent to May 17, 2011 has been disclaimed.

[21] Appl. No.: 238,533

[22] Filed: May 5, 1994

Related U.S. Application Data

[63] Continuation-in-part of Ser. No. 991,335, Dec. 16, 1992, Pat. No. 5,312,586, which is a continuation-in-part of Ser. No. 719,169, Jun. 21, 1991, abandoned.

[51] Int. Cl.$^5$ .......................... A61L 2/18; C02F 1/42; B01J 39/24
[52] U.S. Cl. ...................................... 422/37; 514/840; 210/668
[58] Field of Search .................. 422/28, 37, 292, 159; 514/839, 840; 424/78.04; 210/668

[56] References Cited

U.S. PATENT DOCUMENTS

| | | | |
|---|---|---|---|
| 4,976,921 | 12/1990 | Itagaki et al. | 422/28 |
| 5,312,586 | 5/1994 | Stockel | 422/37 |

*Primary Examiner*—Robert J. Warden
*Assistant Examiner*—E. Leigh Dawson
*Attorney, Agent, or Firm*—Jack Matalon

[57] ABSTRACT

A one-step process for sterilizing a contact lens using an aqueous solution of a sterilant which may be a peroxygen disinfectant, an inorganic hypochlorite compound or a hypochlorite precursor compound. The process involves the step of contacting the lens with a solution containing a sterilant (e.g. hydrogen peroxide, sodium hypochlorite, etc.) and activated carbon for a period of time to effect sterilization of the lens and to decompose substantially all of any sterilant remaining after sterilization of the lens to ophthalmologically innocuous by-products. The activated carbon has a surface area in excess of about 500 $m^2/g$ and a pore volume of at least about 0.75 ml/g.

8 Claims, No Drawings

ONE-STEP CONTACT LENS STERILIZATION PROCESS

REFERENCE TO RELATED APPLICATION

This application is a continuation-in-part of patent application Ser. No. 07/991,335 filed Dec. 16, 1992, now U.S. Pat. No. 5,312,586 issued May 17, 1994, which in turn is a continuation-in-part of patent application Ser. No. 07/719,169 filed Jun. 21, 1991, now abandoned.

FIELD OF THE INVENTION

The present invention relates to a one-step process for sterilizing a contact lens. More particularly, the invention relates to a process for sterilizing a contact lens by the step of contacting the lens with a solution containing a sterilant and activated carbon for a period of time to effect sterilization of the lens and to decompose substantially all of any sterilant remaining after sterilization of the lens to ophthalmologically innocuous by-products.

BACKGROUND OF THE INVENTION

Processes for sterilization of contact lenses are well known in the prior art. Typically such processes employ aqueous solutions of sterilants such as $H_2O_2$ present in a concentration of 1–5 wt. %, together with adjuvants such as chelating agents (e.g. ethylenediaminetetraacetic acid), buffering agents such as alkali metal phosphates, alkali metal borates, alkali metal carbonates and mixtures thereof, etc.

After a contact time sufficient to disinfect the lens, the residual sterilant must be neutralized, i.e. converted into ophthalmologically innocuous by-products, since even traces of the sterilant remaining on the lens will result in irritation to the eye and concomitant discomfort to the contact lens wearer.

It is well known that hydrogen peroxide as a contact lens sterilant is advantageous in that it is capable of being sterilized to only water and oxygen. However such advantage is lost if neutralization is incomplete or if the neutralization agent introduces other reaction products.

Ocular exposure to 3 wt. % (the typical concentration employed for contact lens sterilization) can result in stinging tearing, hyperemia, blepharospasm, edema and possible permanent corneal damage. Indeed clinical laboratory reports have suggested that symptoms of irritation can occur at concentrations as low as 30 ppm. Clinical findings suggest that an ideal solution would be one wherein residual levels of the sterilant may be reduced to near zero concentration while avoiding introducing any spurious contaminants into the disinfecting solution after disinfection.

At the present time, there is no commercially available, approved water-soluble chlorine-based compound employed as a contact lens sterilant. This may be due to the lack of any suitable technology which will result in the neutralization of the residual sterilant to an acceptable level within a reasonable period of time (e.g. 4–8 hours) without the introduction of extraneous chemicals.

Several hydrogen peroxide-based solution have been commercialized for disinfection of contact lenses. With the exception of the platinum-based catalyst system, all other systems create by-products which can become a source of irritation to ocular tissue upon repeated usage. Such systems utilize the following reducing agents to neutralize hydrogen peroxide:

catalase sodium pyruvate sodium thiosulfate

The most common method for neutralizing $H_2O_2$ involves the use of a thin film of platinum on a plastic substrate, as disclosed in U.S. Pat. No. 3,912,451. Such prior art process suffers from several disadvantages. Firstly, this process is quite expensive, owing to the use of platinum. Of course, the device may be reused a number of times (up to a maximum of ~100 times), but frequently the user continues to use the device well after the recommended maximum number of times, either because of inadvertence or to try to achieve further cost savings. Further, after prolonged contact times, high levels of hydrogen peroxide persist with concentrations of 30 ppm not being uncommon. e.g. see the article by J. Z. Krezanoski et al., *J. Amer. Optometric Assoc.*, vol. 59, no. 31, p. 193 (1988). Moreover, the decomposition rate of the residual hydrogen peroxide is non-reproducible and will gradually diminish, thus affording a lack of certainty as to the continued effectiveness of the device. Finally, there is also the need to dispose of an environmentally unfriendly material, i.e. platinum coated on a plastic substrate, since the device is not readily recyclable.

The prior art also teaches that chemical reducing agents, e.g. sodium thiosulfate, may be used to neutralize the residual $H_2O_2$, see A. R. Gasset et al., *Arch. Ophthalmol.*, vol. 93, June, 1975, pp. 412–415. It is also known to utilize a controlled-release sterilant system utilizing sodium percarbonate, see U.S. Pat. No. 4,863,627. However, such techniques are disadvantageous in that they introduce foreign substances which cause a change in the osmotic pressure of the ophthalmological solution and also a severe burning sensation in the eye or even irritation to the ocular tissue may result.

It is also known to use aqueous solutions of inorganic hypochlorites, i.e. alkali and alkaline metal hypochlorites as the sterilants for contact lenses together with reducing agents to neutralize the residual hypochlorite, see U.S. Pat. Nos. 3,717,580 and 4,167,561, Canadian Patent 1,087,955 and U.K. Patent 2,094,922. U.S. Pat. No. 4,976,921 extends the concept of hypochlorite sterilants to compounds which are hypochlorite precursors, e.g. Chloramine-B, Chloramine-T, Dichloramine-T, Halazone, chlorinated cyanuric acid, etc. It is also known that various reducing agents may be used to neutralize the residual hypochlorite precursors, e.g. sodium thiosulfate, $\alpha$- and $\beta$-hydroxy-carboxylic acids such as glycolic, malic, citric, lactic, tartaric, ascorbic, etc.

In many of the systems which employ slow-release inorganic hypochlorite or hypochlorite precursor compounds, a continuous loss of hypochlorite occurs which then entails higher concentrations of hypochlorite than otherwise needed. Such a situation may readily result in misuse by the consumer. Moreover, animal studies have shown that the use of hydroxy-carboxylic acids in the reduction of hypochlorites indicate that the reaction between these reactants produce physiologically irritating and perhaps toxic oxidation by-products, thereby limiting the usefulness of this method. In addition, all presently known methods of reducing hypochlorites bring about a concurrent change in the tonicity of the resulting aqueous solution, thereby causing discomfort to the contact lens wearer.

The present invention overcomes the various problems and disadvantages recited above and offers the following advantages: non-toxic, environmentally safe, disposable, renewable resource, results in substantially complete neutralization, no introduction of spurious additives nor formation of reaction by-products, decomposes hydrogen peroxide to water and oxygen, decomposes hypochlorites to the chloride salt and oxygen, no restrictions are imposes on components to be used in the sterilant formulation when the pH is typically between 6 and 8 and the activated carbon is inexpensive.

SUMMARY OF THE INVENTION

The present invention pertains to a process for sterilizing a contact lens such that the lens is sterilized and any sterilant remaining after the lens is sterilized (herein referred to as "residual" sterilant) is converted to ophthalmologically innocuous by-products in a single step. That is, the sterilant and the activated carbon for neutralization of the residual sterilant are both present at the outset. The present one-step process differs from the two-step process of parent application Ser. No. 07/991,335 wherein in the first step, the lens is sterilized with an aqueous solution containing the sterilant and after sufficient contact time to insure sterilization of the lens, and in a second step, the activated carbon for neutralizing the residual sterilant is added to the resultant aqueous solution.

DETAILS OF THE INVENTION

The process of the invention comprises contacting the lens with (a) about 5 to 25 ml of an aqueous solution containing a sterilant and (b) activated carbon. The sterilant is selected from the group consisting of:
  (i) about 1 to 5 wt. %, based on the weight of the aqueous solution, of a peroxygen disinfectant;
  (ii) about 0.0005 to 0.5 wt. %, based on the weight of the aqueous solution, of an inorganic hypochlorite compound; and
  (iii) about 0.0005 to 0.5 wt. %, based on the weight of the aqueous solution, of a hypochlorite precursor compound;

The activated carbon is present in an amount of about 0.1 to 1.0 gram per 10 ml of solution and having a surface area in excess of about 500 $m^2/g$ and a pore volume of at least about 0.75 ml/g. The contacting of the lens with the solution and the activated carbon occurs for a period of time sufficient to effect sterilization of the lens and to decompose substantially all of any sterilant remaining after sterilization of the lens to ophthalmologically innocuous by-products. Such contact time will range from about 4 to 8 hours, preferably 5 to 7 hours.

The activated carbon causes the sterilant to decompose into ophthalmologically innocuous by-products. For example, in the case of hydrogen peroxide, the by-products are water and oxygen (which evolves from the aqueous solution) while in the case of sodium hypochlorite, the by-products are sodium chloride and oxygen (which evolves from the aqueous solution). Thus the present invention results in no irritating chemicals nor in any significant increase in tonicity which would otherwise cause discomfort to the contact lens wearer due to a buildup in osmotic pressure of the ocular fluid.

Activated carbon is totally innocuous from a health and environmental point of view. Moreover, it is readily commercially available in many grades, particle sizes and forms and is very inexpensive, thus affording considerable economic savings versus other systems such as platinum coated on a plastic substrate. Such cost savings justify the use of the activated carbon on a one-time basis, thereby insuring consistent reproducibility of the sterilant neutralization reaction and avoiding the uncertainties attendant to the repetitive use of the same reduction system. However, if desired, as many as 50 neutralizations can be effected with the same charge of activated carbon without any significant loss of neutralization activity.

For the purposes of the present invention, the activated carbon must have a surface area in excess of about 500 $m^2/g$ and a pore volume of at least about 0.75 ml/g. It has been found that grades of activated carbon not possessing the requisite surface area and pore volume were ineffective in reducing sterilant levels to ophthalmologically safe levels of <10 ppm after a typical contact time of 6 hours.

The activated carbon may be used in many forms, e.g. powder, granules, sheets, rods, fiber, fabric, beads, extrudates, impregnated or coated on substrates, etc. Preferably, the activated carbon is not used in the form of fines which would come into direct contact with the aqueous solution containing the sterilant to be neutralized (i.e. decomposed or reduced). This may be readily and conveniently accomplished by providing the activated carbon in a container which is sealed except for a membrane which is permeable to the aqueous solution but is impermeable to the activated carbon.

Alternatively, the activated carbon may be encapsulated in a water-swellable polymer (typically having a number average molecular weight of >20,000) which is permeable to the aqueous solution (but from which the activated carbon would not otherwise leach out). Non-limiting examples of useful water-swellable polymers include modified cellulolosics such as ethyl cellulose, methyl cellulose, and the like; poly 2-hydroxymethyl methacrylate; ethylene-vinyl acetate copolymer; polyacrylic acid; polyvinyl alcohol; etc. which may be utilized to form microcapsules completely enclosing the activated carbon. The apparatus and method for manufacturing such microcapsules is well known in the prior, e.g. see U.S. Pat. No. 4,978,483.

Typically the amount of aqueous solution employed in the one-step process is about 5 to 25 ml, preferably 10 to 20 ml, per lens and the amount of activated carbon present in the solution is about 0.1 to 1.0, preferably 0.3 to 0.8, gram per 10 ml of aqueous solution.

Where the sterilant comprises a peroxygen disinfectant, it may be a compound such as hydrogen peroxide (which is preferred), sodium carbonate peroxyhydrate, urea hydrogen peroxide, sodium perborate tetrahydrate, sodium perborate monohydrate, zinc peroxide, salts of Caro's acid such as potassium permonosulphate triple salt, peracetic acid, magnesium monoperoxyphthalate, etc. Such peroxygen disinfectants are well known in the prior art, e.g. see the article "Peroxygen Disinfectants" by M. G. C. Baldry and K. Dickinson in *Specialty Chemicals,* November, 1983, p. 17 et seq. The peroxygen disinfectant is typically present in a concentration in the range of about 1 to 5 wt. %, preferably 2 to 4 wt. %, based on the weight of the aqueous solution.

Where the sterilant comprises an inorganic hypochlorite or hypochlorite precursor compound, the concentration may be considerably less, e.g. 0.0005 to 0.5 wt. %, preferably 0.01 to 0.1 wt. %, based on the weight of the aqueous solution. Examples of suitable inorganic hypochlorites include sodium hypochlorite (which is preferred), potassium hypochlorite, calcium hypochlorite, lithium hypochlorite, etc. Examples of suitable hypochlorite precursor compounds include Chloramine-B, Chloramine-T, Dichloramine-T, Halazone, chlorinated cyanuric acid, etc.

Regardless of which sterilant is employed, it is preferred that pH of the aqueous solution containing such sterilant and activated carbon be about 5 to 9, preferably 6 to 8. Typically, the aqueous solution containing the sterilant and activated carbon will be utilized at room temperature. The temperatures are not critical, but room temperature is most practicable for the contact lens wearer.

The aqueous solution containing the sterilant and the activated carbon may also contain the usual adjuvants, e.g. chelating agents such as ethylenediaminetetraacetic acid which may be present in a concentration of less than about 1 wt. %, based on the weight of the aqueous solution, in order to complex any trace metals present in the solution.

The aqueous solution containing the sterilant and activated carbon may also contain other components taught in the prior art for use in disinfecting contact lenses. For example, the solution may contain either an acid or base to adjust the pH and/or it may contain a tonicity adjusting agent. Acids are usually employed to neutralize alkaline hypochlorites while bases are employed to neutralize peroxygen disinfectants in order to achieve a pH in the range of 5 to 9. Suitable bases include alkali or alkaline earth metal carbonates, borates or phosphates, while suitable acids include benzoic, malic, pyruvic, ascorbic, sorbic, tartaric, fumaric, citric, maleic and adipic. Buffers may also be employed such as alkali metal phosphates, alkali metal borates, alkali metal carbonates and mixtures thereof.

This invention may be better understood with reference to the following examples.

EXAMPLE 1

This example demonstrates the effectiveness of the activated carbon in neutralizing the sterilant to an ophthalmologically safe level, regardless of whether the activated carbon was present as is or was encapsulated.

Sample A consisted of 1 g of activated carbon having a surface area of about 1200 $m^2/g$ and a pore volume of about 1.2 ml/g. Sample B consisted of the same grade of activated carbon, but it was present in an encapsulated form; encapsulation was carried out by treating 10 g of the activated carbon with a 2.0 wt. % solution of poly 2-hydroxymethyl methacrylate and air dried. Sample C was prepared in the same manner as Sample B, except that the activated carbon was treated with a 4.0 wt. % solution of poly 2-hydroxymethyl methacrylate.

One g of each of Samples A, B and C was then evaluated as to its effectiveness in neutralizing 10 ml of a commercial phosphate-buffered 3.0 wt. % hydrogen peroxide aqueous solution (pH of 5.8±0.5) to ophthalmologically safe levels of residual hydrogen peroxide. The residual peroxide content was measured using Merckoquat® 1011 Peroxide Test Strips which are capable of measuring peroxide content at levels of 100 ppm down to 0 ppm. As may be seen from the results in Table I below, the activated carbon as is as well as in an encapsulated form was effective in neutralizing the hydrogen peroxide to a safe level in accordance with FDA guidelines for contact lens disinfection procedures.

TABLE I

| | Residual Peroxide After The Indicated Contact Time | | | |
|---|---|---|---|---|
| | 1 hour | 2 hours | 4 hours | 6 hours |
| Sample A | 100 ppm | 30 ppm | 0 ppm | 0 ppm |
| Sample B | >100 ppm | 100 ppm | 30 ppm | 0 ppm |
| Sample C | >100 ppm | >100 ppm | 100 ppm | 30 ppm |

EXAMPLE 2

This example was carried out to demonstrate the effectiveness of various amounts of activated carbon in neutralizing hydrogen peroxide to an ophthalmologically safe level. Sample A and 10 ml of the same hydrogen peroxide and the same test strip procedure of Example 1 were employed for this example. The results as set forth in Table II below show that the activated carbon is effective throughout the range of 0.1–1.0 gram activated carbon per 10 ml of peroxide solution for neutralizing residual peroxide levels.

TABLE II

| | Residual Peroxide After The Indicated Contact Time | | |
|---|---|---|---|
| Activated Carbon, g | 1 hour | 3 hours | 6 hours |
| 0.1 | >100 ppm | 100 ppm | 20 ppm |
| 0.25 | >100 ppm | 100 ppm | 10 ppm |
| 0.5 | >100 ppm | 30 ppm | 3 ppm |
| 1.0 | >100 ppm | 3 ppm | 0 ppm |

EXAMPLE III

The example provides comparative data showing the effectiveness of a conventional platinum catalyst in neutralizing the same hydrogen peroxide solution as employed in Example I, using the same test strip procedure as in Example I. As may be seen from the results in Table III below, the platinum catalyst was not as effective as the activated carbon of the present invention in neutralizing residual peroxide.

TABLE III

| Residual Peroxide After The Indicated Contact Time | |
|---|---|
| Hours | Residual Hydrogen Peroxide, ppm |
| 0 | 30,000 |
| 1 | >100 |
| 2 | >100 |
| 3 | 100 |
| 4 | 30–100 |
| 5 | 30 |
| 6 | 10–30 |

EXAMPLE 4

This example utilized 10 ml of an aqueous solution of 0.02 wt. % sodium hypochlorite which were added to 10 ml of an aqueous pH 7 solution; the latter solution was prepared by mixing 50 ml of 0.1 molar tris (hydroxy- methyl) aminomethane with 46.6 ml of 0.1 molar HCl and diluting the mixture to 1 liter with distilled water. Residual NaOCl was measured by titration with 0.005 molar $Na_2S_2O_3$ solution at the end of 1, 4 and 6 hours. The results as set forth in Table IV below show that the activated carbon of the present invention is effective in neutralizing hypochlorite-type sterilants to ophthalmologically safe levels.

TABLE IV

| Activated Carbon | | | Residual NaOCl | | |
| --- | --- | --- | --- | --- | --- |
| Amount, g | Surface Area, m²/g | Pore Volume, ml/g | 1 hour | 4 hours | 6 hours |
| 0.9 | 900 | 1.18 | 100 | 40 | 10 |
| 0.7 | 1050 | 0.95 | 100 | 10 | 0 |
| 0.5 | 1000 | 1.20 | 150 | 30 | 0 |

What is claimed is:

1. A process for sterilizing a contact lens which comprises contacting the lens with (a) about 5 to 25 ml of an aqueous solution containing a sterilant and (b) activated carbon, said sterilant being selected from the group consisting of:
   (i) about 1 to 5 wt. %, based on the weight of the aqueous solution, of a peroxygen disinfectant;
   (ii) about 0.0005 to 0.5 wt. %, based on the weight of the aqueous solution, of an inorganic hypochlorite compound; and
   (iii) about 0.0005 to 0.5 wt. %, based on the weight of the aqueous solution, of a hypochlorite precursor compound;

said activated carbon being present in an amount of about 0.1 to 1.0 gram per 10 ml of solution and having a surface area in excess of about 500 m²/g and a pore volume of at least about 0.75 ml/g, the contacting of the lens with the solution and the activated carbon occurring for a period of time sufficient to effect sterilization of the lens and to decompose substantially all of any sterilant remaining after sterilization of the lens to ophthalmologically innocuous by-products.

2. The process of claim 1 wherein the peroxygen disinfectant comprises hydrogen peroxide.

3. The process of claim 1 wherein the inorganic hypochlorite compound comprises sodium hypochlorite.

4. The process of claim 1 wherein the period of time of contact of the lens with the aqueous solution is about 4 to 8 hours.

5. The process of claim 1 wherein the aqueous solution has a pH in the range of about 5 to 9.

6. The process of claim 1 wherein the activated carbon is present in a sealed container having a membrane which is permeable to the aqueous solution but is impermeable to the activated carbon.

7. The process of claim 1 wherein the activated carbon is encapsulated in a water-swellable polymer which is permeable to the aqueous solution but is impermeable to the activated carbon.

8. The process of claim 1 wherein the aqueous solution contains a buffer selected from the group consisting of alkali metal phosphates, alkali metal borates, alkali metal carbonates and mixtures thereof.

* * * * *